United States Patent
Kitano et al.

[11] Patent Number: 5,981,786
[45] Date of Patent: Nov. 9, 1999

[54] PROCESS FOR PRODUCING (METH) ACRYLATE DERIVATIVES

[75] Inventors: Shigeru Kitano, Tsukuba; Toshihiko Ohta, Chita-gun; Hiroshi Suzuki, Oita; Akio Hayashi, Kashiwa; Yoshishige Murata, Tokyo; Kazuo Matsuyama, Gamagoori; Kenichiro Nakamoto, Tsukuba, all of Japan

[73] Assignee: NOF Corporation, Tokyo, Japan

[21] Appl. No.: 09/230,605

[22] PCT Filed: May 28, 1998

[86] PCT No.: PCT/JP98/02357

§ 371 Date: Jan. 27, 1999

§ 102(e) Date: Jan. 27, 1999

[87] PCT Pub. No.: WO98/54194

PCT Pub. Date: Dec. 3, 1988

[30] Foreign Application Priority Data

May 30, 1997 [JP] Japan ..................... 9-142146
Feb. 19, 1998 [JP] Japan ..................... 10-37736

[51] Int. Cl.$^6$ ............... C07F 9/09; C07F 9/10; C07F 9/6574
[52] U.S. Cl. ............... 558/86; 558/131; 558/169
[58] Field of Search ................ 558/86, 131, 169

[56] References Cited

U.S. PATENT DOCUMENTS 4,041,012 8/1977 Albright et al. ............... 558/86
5,741,923 4/1998 Driver et al. ............... 558/131

FOREIGN PATENT DOCUMENTS 58-154591 9/1983 Japan.
8-239394 9/1996 Japan.

*Primary Examiner*—Michael G. Ambrose
*Attorney, Agent, or Firm*—Darby & Darby

[57] ABSTRACT

A process for producing a (meth)acrylate derivative including reacting a compound of formula (1) (wherein $R^1$ is H or $CH_3$; A is $C_1$–$C_{10}$ alkylene; and p is 1 to 10) with a chloro-dioxaphosphorus compound of formula (2) (wherein q is 0 or 1) in the presence of a secondary amine of formula (3) (wherein $R^2$ and $R_3$ are each $C_3$–$C_8$ alkyl, cycloalkyl, $C_6$–$C_9$ aryl, arylalkyl, etc.) to produce a (meth)acrylate derivative of formula (4) and further reacting the same with a tertiary amine of formula (5) (wherein $R^4$, $R^5$ and $R^6$ are each $C_1$–$C_4$ alkyl etc.) to provide a (meth)acrylate derivative of formula (6).

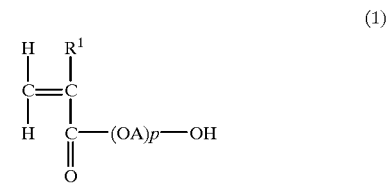

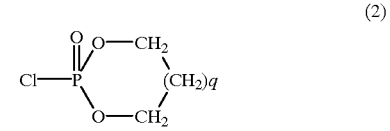

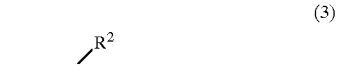

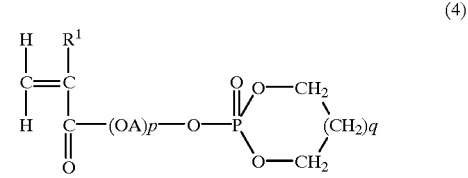

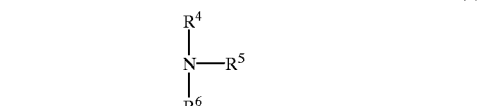

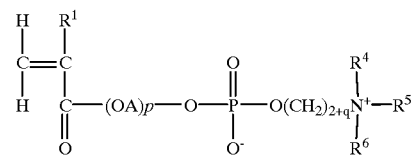

6 Claims, 2 Drawing Sheets

PROCESS FOR PRODUCING (METH) ACRYLATE DERIVATIVES

FIELD OF ART

The present invention relates to a process for producing a (meth)acrylate derivative having a (meth)acrylate group, and either a dioxaphosphorane group or a dioxaphosphorinane group.

BACKGROUND OF ART

Phospholipids are known to be a component of a biomembrane. Phosphatidylcholine, one of phospholipids, is a glycerin ester of a long chain alkylcarboxylic acid having a phosphorylcholine group in polar part thereof.

Recently, some attempts have been made to synthesize a phospholipid-like compound having the phosphorylcholine group. For example, there is known a method for producing the objective phosphorylcholine derivative by reacting 2-chloro-2-oxo-1,3,2-dioxaphosphorane (sometimes referred to hereinbelow as "COP") with a compound having a hydroxyl group in the presence of a tertiary amine such as triethylamine, which acts as hydrogen chloride catcher, to produce 2-oxo-1,3,2-dioxaphosphorane derivative; and then reacting the resulting derivative with trimethylamine (Bull. Soc. Chim. Fr., p667–671, 1974, C. R. Acad. Sc. Paris, t.283 Serie C, p229–231, 1976, Zh. Org. Khim. 16(1), p31–33, 1980, C. R. Acad. Sc. Paris, t.275 Serie C, p1125–1127, (1972)).

There is also known a 2-((meth)acryloyloxy)alkyl-2-(trimethylammonium)ethyl phosphate (sometimes referred to hereinbelow as "(M)APC") having the phosphorylcholine group and a (meth)acryloyl group introduced thereto as a polymerizable group. Methods for producing this "(M)APC" and 2-(2-oxo-1,3,2-dioxyaphosphoryl)alkyl (meth) acrylate, an intermediate product of this "(M)APC" (sometimes referred to hereinbelow as "OP(M)A"), have also been proposed.

For example, it is known that the intermediate product "OPMA" may be produced by reacting 2-hydroxyethyl methacrylate with "COP" in the presence of a tertiary amine, and removing the by-product, that is, hydrochloride of the tertiary amine. It is also known that "MAPC" may be produced by reacting the obtained "OPMA" with a tertiary amine such as trimethylamine (JP-B-2-49316, and WO95/14702 specification). However, in these production methods, it is difficult to sufficiently remove the by-product due to the tertiary amine, which has been used as the hydrogen chloride catcher. In addition, the reaction liquid and the objective "(M)APC" tend to be colored in pale yellow or dark brown. Further, the reaction rate is not sufficiently fast.

Then, it has been proposed to perform reaction under reduced pressure in the absence of a tertiary amine (JP-A-8-239394). However, in this method, hydrogen chloride gas is generated as a result of the reaction under the reduced pressure. It takes a long time to remove the gas. Further the reaction results in low reaction ratio.

It has also been proposed to produce "(M)APC" by reacting 2-hydroxyethyl methacrylate with "COP" using specific acetonitrile in the presence of triethylamine, and then opening the ring by reaction with trimethylamine, and optionally re-crystallizing the product from dry acetonitrile (JP-A-9-505578). However, the coloring of the reaction liquid and the product also occurs in this method. Thus, for producing, e.g., a contact lens by polymerizing the obtained "(M)APC", it is required to perform the step of removing the coloring substance from "(M)APC", such as absorption by activated charcoal, re-crystallization or column chromatography, and the production step cannot therefore be simplified.

DISCLOSURE OF THE INVENTION

The object of the present invention is to provide a process for producing a (meth)acrylate derivative with fast reaction rate, and high yield of the product in high purity.

Another object of the present invention is to provide a process for producing a (meth)acrylate derivative in which coloring of the reaction liquid and product is lowered, and the purification steps can be simplified.

The present inventors made extensive studies for solving the above problems, and found out that it is possible to suppress the generation of by-products including coloring substance and to obtain the objective product at fast reaction rate, by employment of a secondary amine having specific basicity and configuration instead of the tertiary amines which have previously been employed as a hydrogen chloride catcher, to complete the present invention.

That is, according to the present invention, there is provided a process for producing a (meth)acrylate derivative comprising the step of reacting a compound represented by the formula (1):

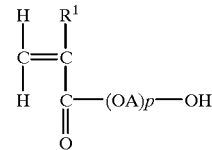

(1)

(wherein $R^1$ denotes a hydrogen atom or a methyl group, A denotes a straight or branched alkylene group having 1 to 10 carbon atoms, and p denotes an integer of 1 to 10) with a chloro-dioxaphosphorus derivative consisting of a chloro-dioxaphosphorane derivative or a chloro-dioxaphosphorinane derivative represented by the formula (2):

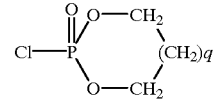

(2)

(wherein q denotes 0 or 1) in the presence of a secondary amine represented by the formula (3):

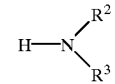

(3)

(wherein $R^2$ and $R^3$ are the same or different groups and denote an isoalkyl, sec-alkyl, tert-alkyl or cycloalkyl group having 3 to 8 carbon atoms, or an aryl or arylalkyl group having 6 to 9 carbon atoms. Alternatively, $R^2$ and $R^3$ may be connected with each other to form a ring), to form a (meth)acrylate derivative represented by the formula (4):

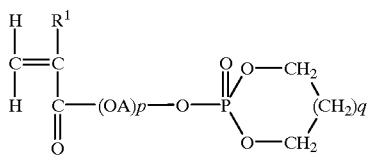
(4)

(wherein $R^1$, A, p and q are the same as $R^1$, A, p and q in the formulae (1) and (2)) (this process is referred to hereinbelow as the first production process of the present invention).

According to the present invention, there is also provided a process for producing a (meth)acrylate derivative comprising the steps of reacting a compound represented by the formula (1) with a chloro-dioxaphosphorus derivative represented by the formula (2) (sometimes referred to hereinbelow as "derivative represented by the formula (2)") in the presence of a secondary amine represented by the formula (3) to produce a (meth)acrylate derivative represented by the formula (4), and reacting the obtained (meth)acrylate derivative with a tertiary amine represented by the formula (5):

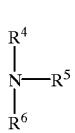
(5)

(wherein $R^4$, $R^5$ and $R^6$ are the same or different groups, and denote an alkyl group having 1 to 4 carbon atoms, which may be connected with each other to form a ring), to produce a (meth)acrylate derivative represented by the formula (6):

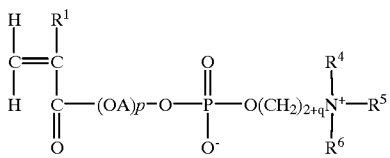
(6)

(wherein $R^1$, A, p and q are the same as $R^1$, A, p and q in the formula (1), and $R^4$, $R^5$ and $R^6$ are the same as $R^4$, $R^5$ and $R^6$ in the formula (5)) (this process is referred to hereinbelow as the second production process of the present invention).

PREFERRED EMBODIMENTS OF THE INVENTION

Figure 1:
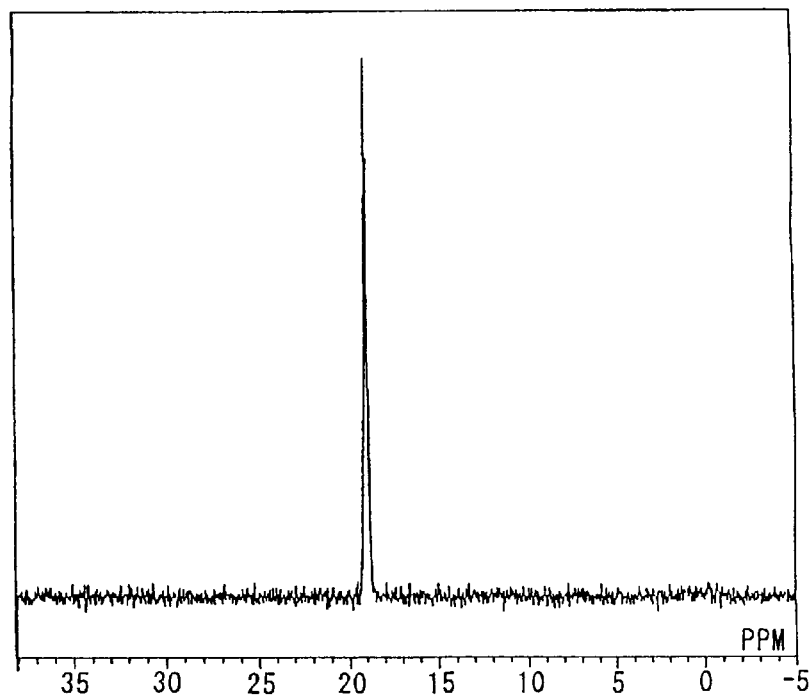
FIG. 1 is a graph showing the result of $^{31}$P-NMR measured in Example 1—1.

In the first and second production processes of the present invention, the examples of the compound represented by the formula (1) used as the starting material may include, e.g., 2-hydroxyethyl (meth)acrylate, 3-hydroxypropyl acrylate, 3-hydroxy-2-methylpropyl methacrylate, diethylene glycol mono(meth)acrylate, triethylene glycol mono(meth)acrylate, tetraethylene glycol mono(meth)acrylate, pentaethylene glycol mono(meth)acrylate, hexaethylene glycol mono(meth)acrylate, dipropylene glycol mono(meth)acrylate, tripropylene glycol mono(meth)acrylate, tetrapropylene glycol mono(meth)acrylate, pentapropylene glycol mono(meth)acrylate, hexapropylene glycol mono(meth)acrylate, isobutylene glycol mono(meth)acrylate, tetramethylene glycol mono(meth)acrylate, hexamethylene glycol mono(meth)acrylate, octamethylene glycol mono(meth)acrylate, decylmethylene glycol mono(meth)acrylate, polyisobutylene glycol mono(meth)acrylate, and polytetramethylene glycol mono(meth)acrylate.

In the derivative represented by the formula (2) which is reacted with the compound represented by the formula (1) in the first and second production processes of the present invention, q is 0 or 1. Particularly, when q=0, the derivative is 2-chloro-2-oxo-1,3,2-dioxaphosphorane (COP) represented by the formula (7):

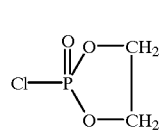
(7)

All of the derivatives represented by the formula (2) in which q is 0 or 1 may be produced by the method of R. S. Edmundson described in "Chemistry and Industry" (Oct. 20, (1962), p1828).

In the first and second production processes of the present invention, the compound represented by the formula (1) is reacted with the derivative represented by the formula (2) in the presence of the secondary amine represented by the formula (3). The secondary amine represented by the formula (3) acts as the hydrogen chloride catcher.

The examples of the secondary amine represented by the formula (3) may include, e.g., diisopropylamine, diisobutylamine, di-sec-butylamine, di-tert-butylamine, diisoheptylamine, di-sec-heptylamine, di-tert-heptylamine, diisohexylamine, di-sec-hexylamine, di-tert-hexylamine, diisooctylamine, di-sec-octylamine, di-tert-octylamine, dicyclohexylamine, N-tert-butyl isopropylamine, N-tert-butyl isobutylamine, diphenylamine, dibenzylamine, and dineopentylamine. Particularly preferable are diisopropylamine, di-sec-butylamine, di-tert-butylamine and diisooctylamine. These secondary amines may be used solely or as mixtures.

In the first and second production processes of the present invention, the reaction of the compound represented by the formula (1) with the derivative represented by the formula (2) in the presence of the secondary amine represented by the formula (3) may be performed, e.g., in accordance with the following procedures: (A) dissolving the compound represented by the formula (1) and the secondary amine represented by the formula (3) in a solvent to prepare a solution, adding the solution dropwise to a mixed solution of the derivative represented by the formula (2) and the solvent, and then stirring the mixture to promote the reaction; and (B) mixing the derivative represented by the formula (2) with a solvent to prepare a mixed solution, and adding the mixed solution dropwise to a solution which have been prepared by dissolving the compound represented by the formula (1) and the secondary amine represented by the formula (3) in the solvent.

In the reaction, preferable introducing molar ratio of the components, that is, the molar ratio of the compound represented by the formula (1): the derivative represented by the formula (2): the secondary amine represented by the formula (3), is in a range of 1:0.75–2:0.75–2, and particularly 1:0.8–1.2:1.0–1.5.

The examples of the solvent for the reaction may preferably include tetrahydrofuran (abbreviated hereinbelow as "THF"), diethyl ether, acetonitrile (abbreviated hereinbelow as "MeCN"), ethyl acetate (abbreviated hereinbelow as "AcEt"), chloroform ($CHCl_3$) and methylene chloride. The amount of the solvent is not particularly limited. However, the preferable amount is usually in a range of 50 to 300 volume %/weight with respect to the derivative represented by the formula (2).

In the reaction, the temperature of the solvent during the dropwise addition is preferably controlled in a range of −50 to 20° C., and particularly −20 to 5° C. After finishing the dropwise addition, it is desirable to continue the reaction under stirring at about the ordinary temperature. Preferable reaction time is 1 to 12 hours, and particularly 2 to 5 hours.

This reaction results in the (meth)acrylate derivative represented by the formula (4). Particularly, when "COP" represented by the formula (7) (q=0) is employed as the derivative represented by the formula (2), the product will be a (meth)acrylate derivative represented by the formula (8):

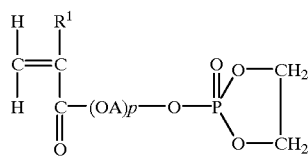

(8)

(wherein A and p are the same as A and p of the formula (1)).

The (meth)acrylate derivative represented by the formula (4) (including the formula (8)) may be 2-(2-oxo-1,3,2-dioxaphosphorane-2-yloxy)ethyl (meth)acrylate, 2-(2-oxo-1,3,2-dioxaphosphorane-2-yloxy)diethoxyethyl (meth)acrylate, 2-(2-oxo-1,3,2-dioxaphosphorinane-2-yloxy)ethyl (meth)acrylate, or 2-(2-oxo-1,3,2-dioxaphosphorinane-2-yloxy)ethoxyethyl (meth)acrylate.

In the reaction for producing the (meth)acrylate derivative represented by the formula (4), a hydrochloride of the secondary amine is generated simultaneously. However, this by-product precipitates, and therefore can be removed easily by, e.g., filtration.

In the second production process of the present invention, the obtained (meth)acrylate derivative represented by the formula (4) is further reacted with the tertiary amine represented by the formula (5), to obtain the (meth)acrylate derivative represented by the formula (6).

The examples of the tertiary amine represented by the formula (5) may include, e.g., trimethylamine, triethylamine, tripropylamine, tributylamine, ethyleneimine, and pyrrolidine.

The reaction of the (meth)acrylate derivative represented by the formula (4) with the tertiary amine represented by the formula (5) may be performed by mixing the components in a solvent, followed by stirring or shaking at a temperature of about 0 to 80° C. for several hours to tens of hours.

In this reaction, preferable introducing molar ratio of the (meth)acrylate derivative represented by the formula (4) and the tertiary amine represented by the formula (5) is 0.5 to 5 moles of the tertiary amine represented by the formula (5) with respect to one mole of the (meth)acrylate derivative represented by the formula (4).

The examples of the solvent for the reaction may include "MeCN", "THF", acetone, "AcEt" and $CHCl_3$. It is preferable to use the same solvent as the solvent used upon reacting the compound represented by the formula (1) with the derivative represented by the formula (2). Employment of "MeCN", "THE" or "AcEt" brings about precipitation and crystallization of the objective product as the reaction proceeds, since the objective (meth)acrylate derivative represented by the formula (6) is not soluble in such solvents. Alternatively, if a solvent in which the objective product dissolves is employed, the objective product can be precipitated and purified by adding the reacted liquid to a large amount of a solvent in which the objective product does not dissolve, such as acetone, after the reaction.

The examples of the (meth)acrylate derivative represented by the formula (6) may include 2-((meth)acryloyloxy)ethyl-2-(trimethylammonium)ethyl phosphate, 2-((meth)acryloyldiethoxy)ethyl-2-(trimethylammonium) ethyl phosphorylcholine, 2-((meth)acryloyloxy)ethyl-2-(trimethylammonium)propyl phosphate and 2-((meth) acryloylethoxy)ethyl-2-(trimethylammonium)propyl phosphate.

In the first production process of the present invention, the reaction is performed using the specific secondary amine instead of the tertiary amine, and therefore the (meth)acrylate derivative represented by the formula (4) containing a small amount of coloring substance can be obtained rapidly with small amount of by-products, with fast reaction rate and high yield. In the second production process of the present invention in which this (meth)acrylate derivative represented by the formula (4) is used as an intermediate product, the purification step can be simplified, and the (meth)acrylate derivative represented by formula (6) can be obtained as white crystals with high yield and high purity.

EXAMPLES OF THE INVENTION

The present invention will be described more in detail with reference to the Examples and Comparative Examples. However, the present invention is not limited thereto.

Example 1—1

A 3 liter reaction vessel equipped with a temperature sensor, a dropping vessel, a stirrer and a thermostatic jacket, was charged with 142.5 g (1 mol) of "COP" and 1500 ml of "THF" as a solvent. The mixture was cooled to 2° C. Then, the dropping vessel was charged with 130.1 g (1 mol) of 2-hydroxyethyl methacrylate (abbreviated hereinbelow as "HEMA"), 101.2 g (1 mol) of diisopropylamine and 500 ml of "THF". The mixture in the dropping vessel was added dropwise to the reaction vessel over 3 hours. After finishing the dropwise addition, reaction was performed at 5° C. for 1 hour and then at 20° C. for 2 hours. After finishing the reaction, precipitated by-product, i.e. hydrochloride of diisopropylamine, was filtered off. The solvent was distilled off, to obtain 2-(2-oxo-1,3,2-dioxaphosphorane-2-yloxy) ethyl methacrylate (abbreviated hereinbelow as "OPMA-1"). The yield was 95%. The purity was 98.5%. The measurement of conversion ratio and purity of "OPMA-1" were made by sampling of the reaction liquid and $^{31}$P-NMR analysis. The results are shown in FIG. 1 and Table 1.

$^{31}$P-NMR was performed using "JEOL JNM-EX270" (manufactured by JEOL LTD.) at 270 MHz. Purity was calculated from the ratio of integral area of "OPMA-1" (18.5 to 19.5 ppm) with respect to the total area of the detected peaks. The results are shown in Table 1.

Evaluation of coloring of "OPMA-1" was made in accordance with JIS K0071 (1993) "test method for color and sulfuric acid coloring of chemical products". During the reaction, reacting liquid of "OPMA-1" was taken out, filtered for removing the hydrochloride of the amine, to prepare a liquid sample. The sample was put in a colorimeter tube (diameter 10 mm), and evaluated in accordance with Hazen unit color number by visual comparison with standard Hazen matching solution. The results are shown in Table 1.

Comparative Examples 1—1 to 1-3

Figure 2:
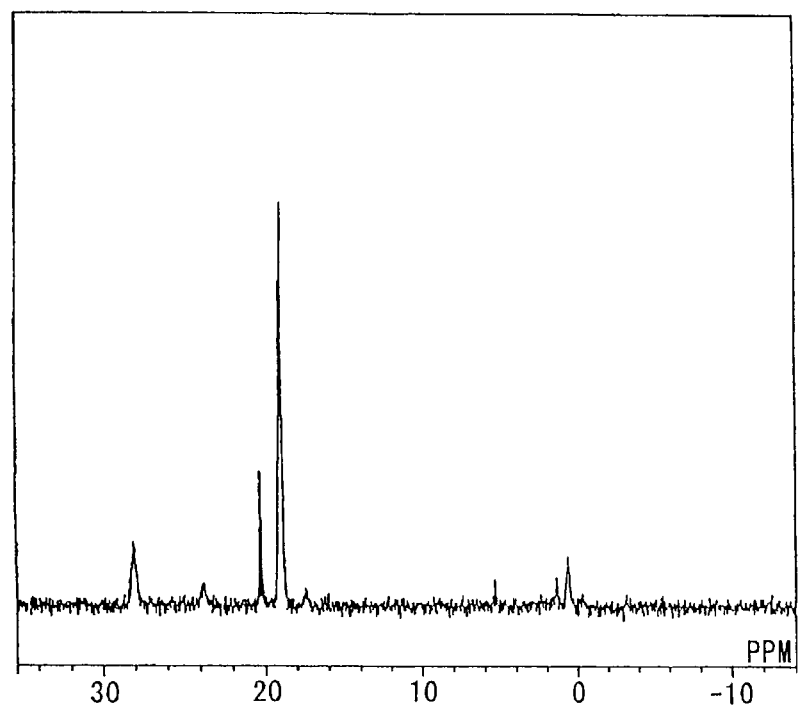
FIG. 2 is a graph showing the result of $^{31}$P-NMR measured in Comparative Example 1—1.
Figure 3:
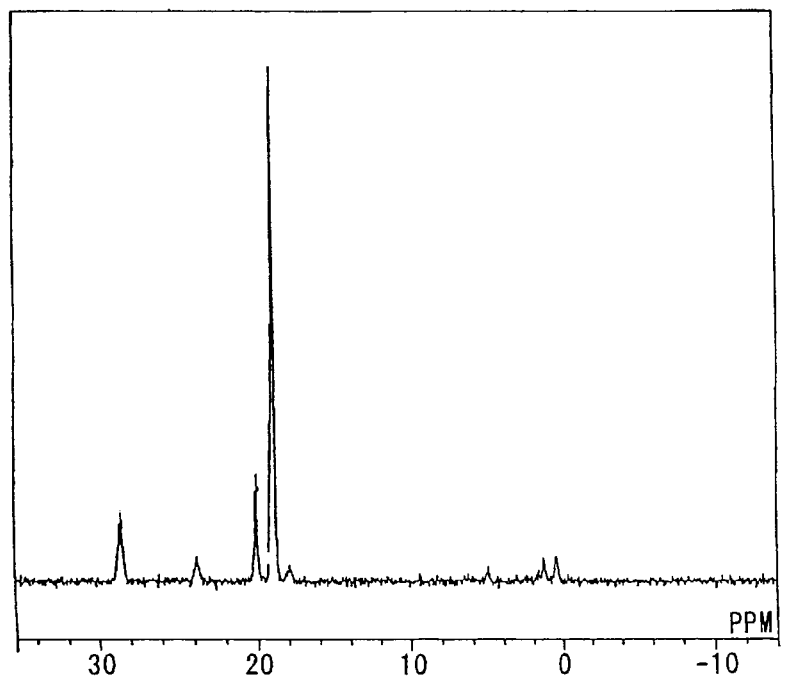
FIG. 3 is a graph showing the result of $^{31}$P-NMR measured in Comparative Example 1-2.
Figure 4:
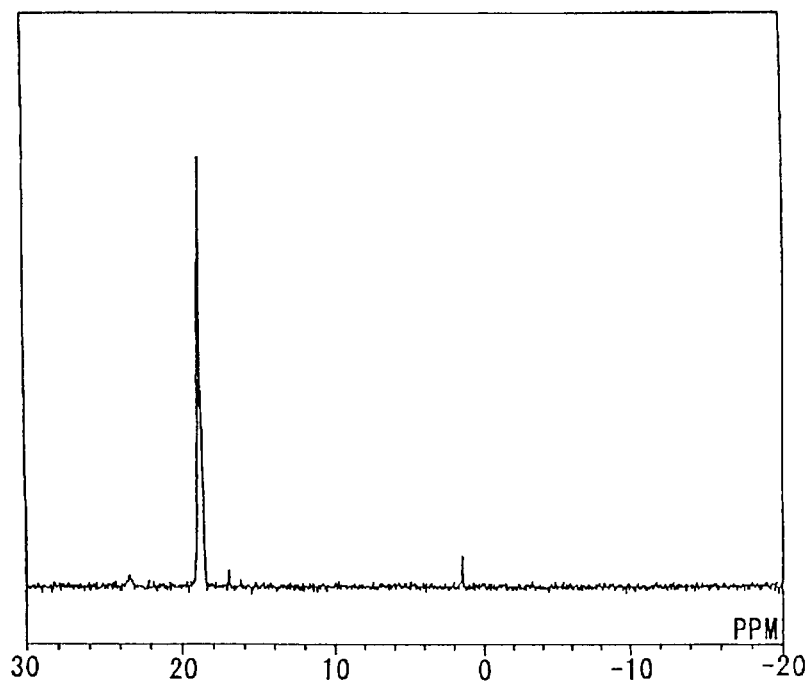
FIG. 4 is a graph showing the result of $^{31}$P-NMR measured in Comparative Example 1-3.

"OPMA-1" was produced in the same way as in Example 1—1 except that 73.1 g (1 mol) of diethylamine (secondary amine, Comparative Example 1—1), 129.3 g (1 mol) of dibutylamine (secondary amine, Comparative Example 1-2), or 101.2 g (1 mol) of triethylamine (tertiary amine, Comparative Example 1-3) was used instead of 101.2 g (1 mol) of diisopropylamine. Measurements and evaluations were also performed. The results are shown in Table 1. The results of $^{31}$P-NMR analysis are shown in FIG. 2 (Comparative Example 1—1), FIG. 3 (Comparative Example 1-2) and FIG. 4 (Comparative Example 1-3), respectively.

TABLE 1

| | Example | Comparative Examples | | |
|---|---|---|---|---|
| | 1-1 | 1-1 | 1-2 | 1-3 |
| Starting materials | | | | |
| Amount of HEMA (g) | 130.1 | 130.1 | 130.1 | 130.1 |
| Amount of COP (g) | 142.5 | 142.5 | 142.5 | 142.5 |
| Sort of amine | diiso propyl amine | di ethyl amine | di butyl amine | tri ethyl amine |
| Amount of amine (g) | 101.2 | 73.1 | 129.3 | 101.2 |
| Solvent | | | | |
| THF (liter) | 2 | 2 | 2 | 2 |
| Conditions | | | | |
| HEMA/COP/Amine (molar ratio) | 1/1/1 | 1/1/1 | 1/1/1 | 1/1/1 |
| Reaction temperature (° C.) | 5 | 5 | 5 | 5 |
| Converting ratio to OPMA (%) | | | | |
| Reaction time | | | | |
| 2 hours | 99.0 | 22.5 | 31.2 | 94.5 |
| 4 hours | — | 38.1 | 47.7 | 95.2 |
| 6 hours | — | 49.8 | 58.9 | 95.6 |
| 8 hours | — | 59.7 | 65.5 | 95.8 |
| Purity of OPMA after removing solvent | 98.5% | 59.0% | 65.2% | 95.0% |
| Color number (Hazen) of reacted liquid | 35 | 40 | 35 | 80 |

From the results in Table 1, it is found that the products having higher purity was obtained at a faster reaction rate with higher yield in Example 1—1 in which the secondary amine was used, compared to the Comparative Examples in which the tertiary amines were used. It is also found that the low coloring of the product was achieved in Example 1—1.

Example 2-1

224 g (0.95 mol) of "OPMA-1" synthesized in Example 1—1 was transferred to a pressure vessel equipped with an airtight plug, and admixed with 1200 ml of "MeCN" and 118 g (2 mol) of trimethylamine. The airtight plug was closed and the reaction was stirred at 60° C. for 12 hours. Excess trimethylamine was distilled off. The reaction was left at 5° C. for 24 hours. The generated crystals were taken by filtration in a dry box, and dried under reduced pressure, to obtain 259 g of the final product, 2-(methacryloyloxy)ethyl-2-(trimethylammonium)ethyl phosphate (abbreviated hereinbelow as "MAPC-1") as white crystals. The yield was 95%.

The obtained "MAPC-1" was admixed with distilled water to prepare a 15 wt % aqueous solution. For this solution, the Hazen unit color number was measured in the same way as in Example 1—1. The results are shown in Table 2.

Comparative Examples 2-1 to 2-3

Using "OPMA-1" synthesized in Comparative Examples 1—1 to 1-3, the final product "MAPC-1" was synthesized and evaluated in the same way as in Example 2-1. The yields, yielding ratio, and resulting Hazen unit color numbers are shown in Table 2. In Comparative Example 2-1, white crystal of "MAPC-1" was not obtained.

TABLE 2

| | Example | Comparative Examples | | |
|---|---|---|---|---|
| | 2-1 | 2-1 | 2-2 | 2-3 |
| Generation of crystal | Yes | No | Yes | Yes |
| Yield (g) | 259 | — | 124 | 232 |
| Yielding ratio (%) | 95 | — | 46 | 85 |
| Color number (Hazen) of 15 wt % aqueous solution | 60 | — | 70 | 150 |

From the results in Table 2, it is found that the objective "MAPC-1" was obtained with higher yield and lower coloration in Example 2-1 employing "OPMA-1" obtained in Example 1—1 than those in any of Comparative Examples.

Comparative Referential Example 1

To 50 ml of 15 wt % aqueous solution of "MAPC-1" synthesized in Comparative Example 2-3, 0.5 g of activate charcoal particles were added. The mixture was stirred at the ordinary temperature for 120 minutes. After finishing stirring, the mixture was left at a stand, and then filtered through a No. 5C filter to remove the activated charcoal, for obtaining a solution of decolorized "MAPC-1". For this solution, Hazen color number was measured. The results are shown in Table 3.

Comparative Referential Example 2

To 50 ml of 15 wt % aqueous solution of "MAPC-1" synthesized in Comparative Example 2-3, 1 g of activated clay (trade name "KYO WAADO® 700" manufactured by Kyowa Chemical Industry Co. Ltd.) was added. The mixture was stirred at the ordinary temperature for 120 minutes. After finishing stirring, the mixture was left at a stand, and then filtered through a No. 5C filter to remove the activated clay, for obtaining a solution of decolorized "MAPC-1". For this solution, Hazen color number was measured. The results are shown in Table 3.

TABLE 3

|  | Example | Comparative Example | Comparative Referential Examples | |
|---|---|---|---|---|
|  | 2-1 | 2-3 | 1 | 2 |
| Color number (Hazen) of 15 wt % aqueous solution | 60 | 150 | 70 | 100 |

From the results in Table 3, it is found that the evaluations in both Comparative Referential Examples 1 and 2, in which "MAPC-1" synthesized in Comparative Example 2-3 was decolorized, were inferior to the coloring evaluation of Example 2-1.

Example 3-1

The reaction was performed in the same way as in Example 1—1 except that 174.2 g (1 mol) of diethylene glycol monomethacrylate (abbreviated hereinbelow as "DEGMA") was employed instead of 130.1 g (1 mol) of "HEMA", to obtain 2-(2-oxo-1,3,2-dioxaphosphorane-2-yloxy)diethoxyethyl methacrylate. For the product, measurements were performed in the same way as in Example 1—1. The results are shown in Table 4.

Example 3-2

The reaction was performed in the same way as in Example 1—1 except that 218.2 g (1 mol) of triethylene glycol monomethacrylate (abbreviated hereinbelow as "TEGMA") was employed instead of 130.1 g (1 mol) of "HEMA", to obtain 2-(2-oxo-1,3,2-dioxaphosphorane-2-yloxy)diethoxyethyl methacrylate. For the product, measurements were performed in the same way as in Example 1—1. The results are shown in Table 4.

Comparative Example 3-1

The reaction was performed in the same way as in Example 1—1 except that 174.2 g (1 mol) of "DEGMA" was employed instead of 130.1 g (1 mol) of "HEMA", and that 101.2 g (1 mol) of triethyleneamine was employed instead of 101.2 g (1 mol) of diisopropylamine. For the product, measurements were performed in the same way as in Example 1—1. The results are shown in Table 4.

Comparative Example 3-2

The reaction was performed in the same way as in Example 1—1 except that 218.2 g (1 mol) of "TEGMA" was employed instead of 130.1 g (1 mol) of "HEMA", and that 101.2 g (1 mol) of triethyleneamine was employed instead of 101.2 g (1 mol) of diisopropylamine. For the product, measurements were performed in the same way as in Example 1—1. The results are shown in Table 4.

TABLE 4

|  | Examples | | Comparative Examples | |
|---|---|---|---|---|
|  | 3-1 | 3-2 | 3-1 | 3-2 |
| Starting materials | | | | |
| Sort of polymerizable compounds | DEGMA | TEGMA | DEGMA | TEGMA |
| Amount (g) | 174.2 | 218.2 | 174.2 | 218.2 |
| Amount of COP (g) | 142.5 | 142.5 | 142.5 | 142.5 |
| Sort of amines | Diiso propyl amine | Diiso propyl amine | Tri ethyl amine | Tri ethyl amine |
| Amount of amine (g) | 101.2 | 101.2 | 101.2 | 101.2 |
| Solvent | | | | |
| THF (liter) | 2 | 2 | 2 | 2 |
| Condition | | | | |
| Polymerizable compound/COP/amine (molar ratio) | 1/1/1 | 1/1/1 | 1/1/1 | 1/1/1 |
| Reaction Temperature (° C.) | 5 | 5 | 5 | 5 |
| Converting ratio to the objective compound (%) | | | | |
| Reaction time | | | | |
| 2 hours | 97.7 | 96.5 | 88.6 | 86.4 |
| 4 hours | — | — | 89.1 | 87.7 |
| 6 hours | — | — | 90.4 | 88.1 |
| 8 hours | — | — | 90.6 | 88.1 |
| Purity of product after removing solvent | 97.0% | 96.1% | 89.9% | 88.0% |
| Color number (Hazen) of reacted liquid | 50 | 50 | 70 | 100 |

From the results in Table 4, it is found that products having higher purity was obtained with higher yield and faster reaction rate in Examples 3-1 and 3-2 in which the secondary amine was used, compared to Comparative Examples in which the tertiary amine was used. It is also found that the low level of coloring of the product was achieved in Examples 3-1 and 3-2.

Example 4-1

A 50 liter reaction vessel equipped with a stirrer and a thermometer was charged with 2.14 kg (15 mol) of "COP" and 25 liter of "THF" as a solvent. The mixture was cooled to 5° C. Subsequently, a mixture solution of 1.95 kg (15 mol) of "HEMA", 1.53 kg (15 mol) of diisopropylamine and 5 liter of "THF" was added dropwise to the reaction over 5 hours. Three hours after finishing the dropwise adding, the temperature inside the reaction vessel became equal to that of outside. Hydrochloride of diisopropylamine precipitated was then filtered off. The solvent in the filtrate was distilled off, to obtain 3.40 kg of intermediate product "OPMA-1". The yield was 96%. The purity was 99%. The measurement of conversion ratio and purity of "OPMA-1" were made by sampling of the reaction liquid and $^{31}$P-NMR analysis. The results are shown in Table 5.

Comparative Example 4-1

Reaction was performed in the same way as in Example 4-1 except that 1.53 kg (15 mol) of triethylamine was used instead of 1.53 kg (15 mol) of diisopropylamine. In the reaction process, 9 hours after finishing the dropwise adding, the temperature inside the reaction vessel became equal to that of outside. Hydrochloride of triethylamine precipitated was then filtered off. The solvent in the filtrate was distilled off, to obtain 3.22 kg of intermediate product "OPMA-1". The yield was 91%. The purity was 95%. The results are shown in table 5.

Example 4-2

3.40 kg of "OPMA-1" synthesized in Example 2-1 was transferred to a 50 liter reaction vessel, mixed with 18 liter of "MeCN", and further mixed with 0.89 kg (15 mol) of trimetylamine. The mixture was stirred to react at the ordinary temperature for 40 hours. After finishing the reaction, trimethylamine in excess was removed under reduced pressure. The liquid was left at 5° C. for 24 hours. Crystals generated were separated by filtration, and dried under reduced pressure at the ordinary temperature, to obtain 3.23 kg of the final product "MAPC-1" as white crystals. The yield was 76%. The results are shown in Table 5.

Comparative Example 4-2

Using 3.22 kg of "OPMA-1" synthesized in Comparative Example 4-1, reaction was performed in the same way as in Example 4-2. 2.78 kg of white crystals of the final product "MAPC-1" was obtained. The yield was 69%. The results are shown in Table 5.

TABLE 5

|  | Examples 4-1 4-2 | Comparative Examples 4-1 4-2 |
| --- | --- | --- |
| Dropping time | 5 hours | 5 hours |
| Time for completing OPMA reaction | 3 hours | 9 hours |
| Purity of OPMA (%) | 99 | 95 |
| Yield of OPMA (%) | 96 | 91 |
| Yield of MAPC (%) | 76 | 69 |

From the results in Table 5, it is found that Examples 4-1 and 4-2 resulted in faster reaction rate and higher yield of the product than Comparative Examples 4-1 and 4-2.

What is claimed is:

1. A process for producing a (meth)acrylate derivative comprising the step of reacting a compound represented by the formula (1):

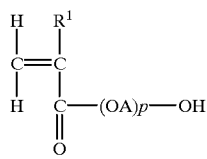
(1)

(wherein $R^1$ denotes a hydrogen atom or a methyl group, and A denotes a straight or branched alkylene group having 1 to 10 carbon atoms, and p denotes an integer of 1 to 10), with a chloro-dioxaphosphorus derivative represented by the formula (2):

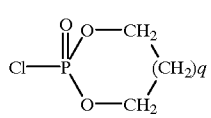
(2)

(wherein q denotes 0 or 1) in the presence of a secondary amine represented by the formula (3):

(3)

(wherein $R^2$ and $R^3$ are the same or different groups and denote an isoalkyl, sec-alkyl, tert-alkyl or cycloalkyl group having 3 to 8 carbon atoms, or an aryl or arylalkyl group having 6 to 9 carbon atoms, alternatively, $R^2$ and $R^3$ may be connected with each other to form a ring), to form a (meth)acrylate derivative represented by the formula (4):

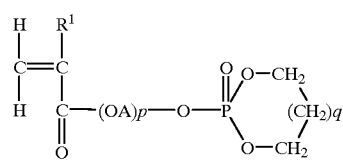
(4)

(wherein $R^1$, A, p and q are the same as $R^1$, A, p and q in the formulae (1) and (2)).

2. The process for producing the (meth)acrylate derivative of claim 1 wherein the introducing molar ratio of the compound represented by the formula (1): the chloro-dioxaphosphorus derivative represented by the formula (2): the secondary amine represented by the formula (3) is 1:0.75–2:0.75–2.

3. The process for producing the (meth)acrylate derivative of claim 1 wherein reaction of the compound represented by the formula (1) with the chloro-dioxaphosphorus derivative represented by the formula (2) is performed in the presence of a solvent, and the temperature of said solvent is controlled in a range of −50 to 20° C.

4. A process for producing a (meth)acrylate derivative comprising the steps of reacting a compound represented by the formula (1):

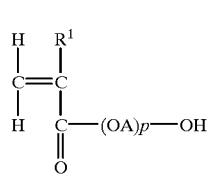
(1)

(wherein $R^1$ denotes a hydrogen atom or a methyl group, A denotes a straight or branched alkylene group having 1 to 10 carbon atoms, and p denotes an integer of 1 to 10) with a chloro-dioxaphosphorus derivative represented by the formula (2):

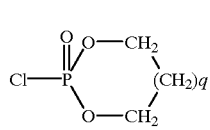
(2)

(wherein q denotes 0 or 1) in the presence of a secondary amine represented by the formula (3):

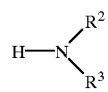
(3)

(wherein $R^2$ and $R^3$ are the same or different groups and denote an isoalkyl, sec-alkyl, tert-alkyl or cycloalkyl group having 3 to 8 carbon atoms, or an aryl or arylalkyl group having 6 to 9 carbon atoms, alternatively, $R^2$ and $R^3$ may be connected with each other to form a ring) to produce a (meth)acrylate derivative represented by the formula (4):

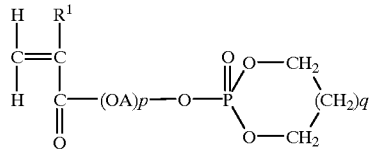
(4)

(wherein $R^1$, A, p and q are the same as $R^1$, A, p and q in the formulae (1) and (2)), and subsequently reacting the obtained (meth)acrylate derivative with a tertiary amine represented by the formula (5):

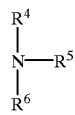
(5)

(wherein $R^4$, $R^5$ and $R^6$ are the same or different groups, and denote an alkyl group having 1 to 4 carbon atoms, which may be connected with each other to form a ring), to produce a (meth)acrylate derivative represented by the formula (6):

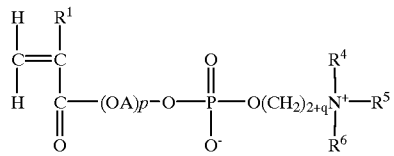
(6)

(wherein $R^1$, A, p and q are the same as $R^1$, A, p and q in the formula (1), and $R^4$, $R^5$ and $R^6$ are the same as $R^4$, $R^5$ and $R^6$ in the formula (5)).

5. The process for producing the (meth)acrylate derivative of claim 4 characterized in that 0.5 to 5 moles of the tertiary amine represented by the formula (5) is introduced per 1 mole of the (meth)acrylate derivative represented by the formula (4) upon reacting the (meth)acrylate derivative represented by the formula (4) with the tertiary amine represented by the formula (5).

6. The process for producing the (meth)acrylate derivative of claim 4 characterized in that reaction of the (meth)acrylate derivative represented by the formula (4) with the tertiary amine represented by the formula (5) is performed in the presence of a solvent at 0 to 80° C. with shaking.

\* \* \* \* \*